United States Patent [19]

Ohtani et al.

[11] Patent Number: 5,117,039
[45] Date of Patent: May 26, 1992

[54] MONOESTERS OF ARYLACETIC ACID AND THE PROCESS THEREOF

[75] Inventors: Mitsuaki Ohtani, Nara; Takaharu Matsuura, Hyogo; Toshiro Konoike, Osaka; Yoshitaka Araki, Hyogo, all of Japan

[73] Assignee: Shionogi & Co., Ltd., Osaka, Japan

[21] Appl. No.: 447,518

[22] Filed: Dec. 7, 1989

[30] Foreign Application Priority Data

Dec. 14, 1988 [JP] Japan .................. 63-315730

[51] Int. Cl.$^5$ ............................................. C07C 69/76
[52] U.S. Cl. ............................................. 560/60
[58] Field of Search ................................ 560/104, 60

[56] References Cited

PUBLICATIONS

CA 109(17):148922s Furuta K. et al Tetrahedion Lett 28(47) 5841-4 1987.

Primary Examiner—Paul J. Killos
Attorney, Agent, or Firm—Wenderoth, Lind & Ponack

[57] ABSTRACT

An optically active ester of arylacetic acid of the fomula:

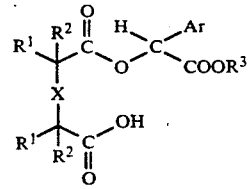

wherein $R^1$ is hydrogen or optionally substituted $C_1$–$C_2$ alkyl or phenyl or taken together to from $C_2$–$C_6$ *alkylene*, or $C_2$ $C_4$–$C_6$ alkenylene, or bicyclic-ring; $R^2$ is hydrogen or methyl; X is single bond or $Ch_2$, C=O, N—$R^4$, O, S, $CHNHR^4$, $CHCH_3$, CH—Ar, or $CHOR^5$ (provided that when X is single bond or $CH_2$, C=O, N—$R^4$, O, or S, $R^1$ and $R^2$ are not simultaneouly hydrogen or methyl); $R^3$ is hydrogen, optionally substituted alkyl, or optionally substituted aralkyl; $R^4$ is hydrogen or amino protecting group; $R^5$ is hydrogen or hydroxy protecting group; and Ar is optionally substituted aryl; prepared by the reaction of a 94 symmetric acid anhydride with an (R)-or (S)-arylacetic acid derivative in high optical purity; useful as a intermediate for the various optically active natural products and medicines.

5 Claims, No Drawings

MONOESTERS OF ARYLACETIC ACID AND THE PROCESS THEREOF

BACKGROUND OF THE INVENTION

1. Field of the Invention

This invention is useful for asymmetric synthesis of various natural products and medicines. More particularly, it relates to arylacetic acid esters useful in preparing optically active prostaglandins and process for the production the said esters.

2. Description of the Prior Art

As to methods for preparing such optically active compounds, Diels-Alder reaction, enzymatic hydrolysis of the diester moiety, or the like is well known. However, such products as prepared by those reactions have generally low optical purity or, even if the optical purity would be high, impurities such as enantiomers are hardly removed. Furthermore, in the aforesaid enzymatic hydrolysis, there are difficulties with the acceptability of the reactant with enzymes or in setting reaction conditions for the enzymes. Therefore, it has been quite difficult to obtain optically pure compounds, economically on a large scale.

It is significant to obtain compounds in a high optical purity by asymmetric synthesis without using an enzyme in synthesis of natural organic compounds as well as in synthesis of various other compounds including medicines in a broad sense.

This invention is intended to provide the optically active intermediates which are useful for the asymmetric syntheses for various optically active compounds, especially medicines in a high purity. This invention also provides processes for preparing optically pure intermediates by promoting the reaction stereoselectively and removing with ease small quantities of by-products resulting in the course of the reaction. This invention is further intended to make it possible to carry out the said reaction easily with inexpensive reagents.

SUMMARY OF THE INVENTION

An optically active ester of arylacetic acid of the formula (II):

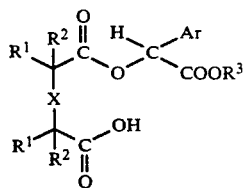

wherein $R^1$ is hydrogen or optionally substituted $C_1$–$C_2$ alkyl or phenyl or taken together to form $C_2$–$C_6$ alkylene, $C_2$ or $C_4$–$C_6$ alkenylene, or bicyclic-ring; $R^2$ is hydrogen or methyl; X is single bond or $CH_2$, C=O, N—$R^4$, O, S, CHNH$R^4$, CHCH$_3$, CH—Ar, or CHO$R^5$ (provided that when X is single bond or $CH_2$, C=O, N—$R^4$, O, or S, $R^1$ and $R^2$ are not simultaneouly hydrogen or methyl); $R^3$ is hydrogen, optionally substituted alkyl, or optionally substituted aralkyl; $R^4$ is hydrogen or amino protecting group; $R^5$ is hydrogen or hydroxy protecting group; and Ar is optionally substituted aryl and, an asymmetric synthesis for preparing the said ester II being characterized by the reaction of a σ symmetric acid anhydride with an (R)- or (S)-arylacetic acid derivative. The ester II which is prepared in high optical purity by the cleavage reaction is useful as an intermediate for the various optically active natural products and medicines.

DESCRIPTION OF THE PREFERRED EMBODIMENTS

In view of the above circumstances, the inventors studied strenuously and as a result, found that a monoester of arylacetic acid having a desired configuration can be prepared selectively by reacting a σ symmetric acid anhydride with an (R)- or (S)-arylacetaic acid derivative. This invention is based on those findings and the details are described later. The by-products yielded in the course of this reaction can be removed by recrystallization. The asymmetric synthetic process provided by this invention can be applied to a wide variety of σ symmetric acid anhydrides. Thus, the obtained monoesters of arylacetic acid are very important as intermediates for preparing various useful natural products such as prostaglandins, macrolides, polyether compounds, macrolactam, aminosugar, nucleotides, terpenes, alkaloids, compactin, and the like naturally derived products. This invention provides such important intermediates as mentioned above, namely esters of arylacetic acid of the formula (II):

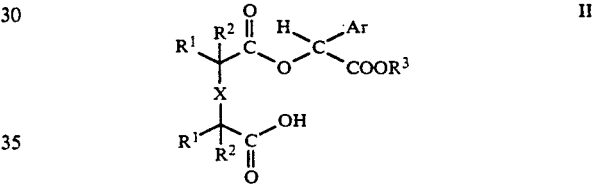

wherein $R^1$ is hydrogen or optionally substituted $C_1$–$C_2$ alkyl or phenyl or taken together to form $C_2$–$C_6$ alkylene, $C_2$ or $C_4$–$C_6$ alkenylene, or bicyclic-ring; $R^2$ is hydrogen or methyl; X is single bond or $CH_2$, C=O, N—$R^4$, O, S, CHNH$R^4$, CHCH$_3$, CH—Ar, or CHO$R^5$ (provided that when X is single bond or $CH_2$, C=O, N—$R^4$, O, or S, $R^1$ and $R^2$ are not simultaneously hydrogen or methyl); $R^3$ is hydrogen, optionally substituted alkyl, or optionally substituted aralkyl; $R^4$ is hydrogen or amino protecting group; $R^5$ is hydrogen or hydroxy protecting group; and Ar is optionally substituted aryl.

This invention further provides processes for asymmetrically preparing esters of arylacetic acids of the formula (II):

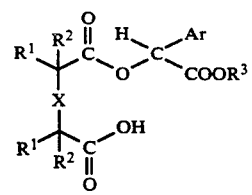

wherein $R^1$, $R^2$, $R^3$, Ar and X, each has the same meaning as defined above, being characterized by the reaction of a σ symmetric acid anhydride of the formula (I):

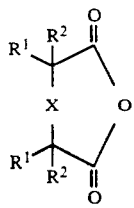

wherein $R^1$, $R^2$, and X, each has the same meaning as defined above, with an (R)- or (S)-arylacetic acid derivative of the formula:

wherein $M^1$ is hydrogen or metal atom; $R^3$ and Ar, each has the same meaning as defined above, and if desired, followed by deprotection.

The compound, in which the carboxyl group of the arylacetic acid moiety is protected, of the formula (II-e):

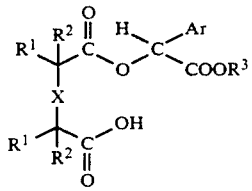

wherein $R^1$, $R^2$, and Ar, each has the same meaning as defined above and $R^{3'}$ is optionally substituted alkyl, or optionally substituted aralkyl, is hardly crystallized and separated from the other by-product, while the corresponding deprotected compound of the formula (II-D) or (II-L)

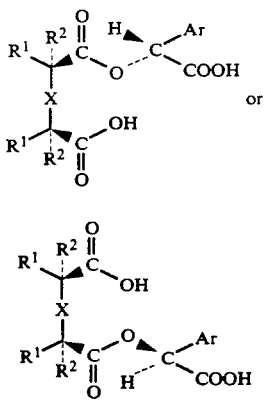

wherein $R^1$, $R^2$, and Ar, each has the same meaning as defined above, can be recrystallized easily and, as a result, can be quite readily isolated as the stereochemically pure compound.

The following reaction schemes illustrate this invention in more detail:

[Method A]
Method using (R)-arylacetic acid derivative

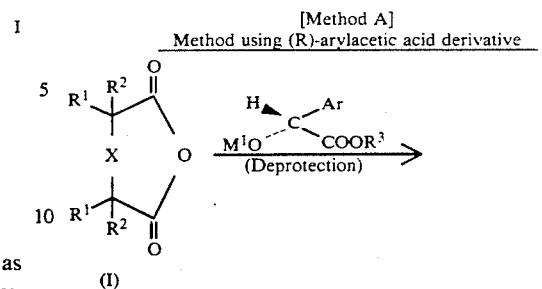

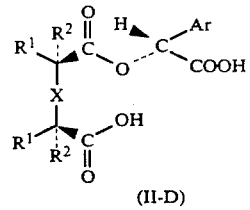

In the reaction scheme, $R^1$, $R^2$, $R^3$, Ar, $M^1$ and X, each has the same meaning as defined above.

A prochiral cyclic anhydride having σ symmetry is allowed to react with (R)-arylacetic acid derivative in a solvent at a temperature from about −100° to about 50° C., preferably from about −100° to about 0° C., for about several tens of minutes to several hours to give to compound (II-De). Usable solvents include tetrahydrofuran, diethyl ether, diisopropyl ether, dioxane, 1,2-dimethoxyethane, n-hexane, DMSO, toluene, and hexamethylphosphoramide (HMPA).

The objective compound (II-D) can be obtained directly when the arylacetic acid derivatives are free acids. On the other hand the compound (II-D) can be obtained via optional deprotection when those are protected form, i.e. arylacetic acid esters. In this specification, the objective compound before the removal of the protective group is sometimes refered to as the compound (II-De). In many cases, the compound (II-De) is not crystallized. However, if it is converted into the objective compound (II-D) by deprotection, the pure product is easily crystallized and isolated. In this process, impurities, especially the compound of the formula (II′-De):

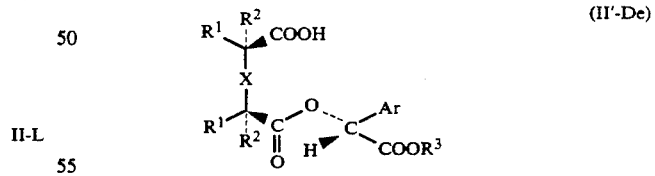

wherein $R^1$, $R^2$, $R^3$, Ar and X, each has the same meaning as defind above resulted in a very small quantity in a course of the reaction, can be removed very easily. The by-product (II′-D) easily obtained by deprotection of the compound (II′-De) stays in the mother liquor and therefore can be removed completely. Thus, the pure objective compound (II-D) can be obtained very easily. A number of methods for asymmetric syntheses have been proposed so far, but no methods, in which diastereomers accompanied as by-product can be so easily removed as in this invention, have been known yet. It is recommended that the deprotection would be performed under neutral or acidic conditions. That is, it is necessary to perform the deprotection without cleaving the ester linkage of the arylacetic acid derivative. If the reaction is performed under alkaline conditions, the ester linkage is broken, so such conditions are not suitable. Usually, the deprotection is carried out under neutral conditions with palladium-carbon. However, those in which there are some other functional groups which are easily reduced or two $R^1$s are taken together to form $C_2$-$C_4$ alkenylene or bicyclic ring having double bond, are sometimes hydrogenated to result in those having a single bond. If it is desired to perform the deprotection, keeping the said functional group, double bond, etc., intact, it is recommended that the deprotection is performed under acidic conditions with the use of such reagents as trifluoroacetic acid, aluminum chloride, hydrochloric acid, or zinc/acetic acid. Depending on types of the substituent $R^3$, suitable conditions may be selected.

[Method B]
Method using (S)-arylacetic acid derivative

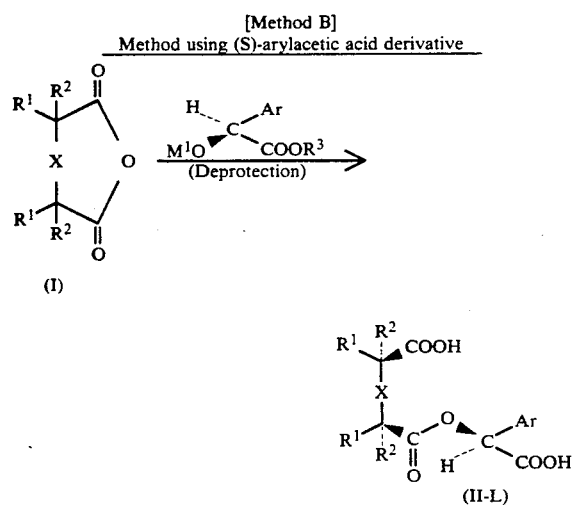

In the reaction scheme, $R^1$, $R^2$, $R^3$, Ar, $M^1$ and X, each has the same meaning as defined above.

The optically pure objective compound (II-L) can be obtained by completely the same procedure as the method A except that (S)-arylacetic acid derivative is used.

In this specification, "optionally substituted $C_1$-$C_2$ alkyl or phenyl" means $C_1$-$C_2$ alkyl or phenyl which may be substituted by lower alkylcarbonyl, lower alkyloxycarbonyl or protected formyl. Here, lower alkyl includes $C_1$-$C_3$ alkyl, such as methyl, ethyl, propyl and isopropyl. Protected formyl includes ethyleneglycol acetal, dimethyl acetal, and diethyl acetal.

$C_2$-$C_6$ alkylene includes ethylene, propylene, butylene, pentylene, or hexylene each of which may have one or more substituents, as long as $\sigma$ symmetry of the acid anhydride is retained.

$C_2$-$C_6$ alkenylene expect $C_3$ includes vinylene, 2-butenylene, 1,3-butadienylene, 1,4-pentadienylene, 3-hexenylene, 2,4-hexadienylene, or 1,5-hexadeenylene, each of which may have one or more substituents, as long as $\sigma$ symmetry of the acid anhydride is retained.

Bicyclic-ring means norbornane type (bicyclo[2,2,1]heptane, bicyclo[2,2,1]hept-5-ene, etc.), 7-oxabicyclo[2,2,1]heptane, 7-oxabicyclo[2,2,1]hept-5-ene, 7-azabicyclo[2,2,1]heptane, 7-azabicyclo[2,2,1]hept-5-ene, 7-thiabicyclo[2,2,1]heptane, 7-thiabicyclo[2,2,1]hept-5-ene, etc.

Carbonyl group (C=O) shown by X may be protected as ketal.

The term "amino protecting group" includes acyl, e.g., formyl, acetyl, benzoyl; urethane type derivative formative group, e.g., benzyloxycarbonyl, tert-butylcarbonyl, 2-(p-biphenyl)isopropoxycarbonyl; ally; benzyl; triphenylmethyl; or tetrahydropyranyl; or the like.

The term "hydroxy protecting group" includes ether formative group; e.g., methyl, tert-butyl, benzyl, allyl, tetrahydropyranyl, tert-butyldimethylsilyl, tert-butyldiphenylsilyl; ester formative group; e.g., acetyl, benzoyl; sulfonate ester formative group e.g., methanesulfonyl, p-toluenesulfonyl, benzenesulfonyl; or the like.

However, the amino protecting group and the hydroxy protecting group are not limited into the examples shown above, it may be selected from the various groups generally employed in the art, for example, those described in "Protective Group in Organic Chemistry" edited by J.F.W. McOmie, Plenum Press, (1973), pp. 43–143.

In the term "optionally substituted aryl", aryl means phenyl or $\alpha$- or $\beta$-naphthyl. As for substituents, there is no particular limitation with the exception of esters. Alkoxy such as methoxy and ethoxy and halogen such as bromine, chlorine and fluorine are exemplified.

Metal atom means alkali metal atoms such as lithium, sodium and potassium; alkaline earth metal atoms such as magnesium and calcium; and zinc.

The term "optionally substituted aralkyl" means benzyl, benzhydryl or naphthylmethyl which may be substituted by alkyl such as methyl, ethyl and propyl; alkoxy such as methoxy, ethoxy and propoxy; halogen such as bromine, chlorine and fluorine. Usable (R)- or (S)-arylacetic acid derivatives in this invention are clear from the above explanation. Among those, however, D- or L-mandelic acid or its derivatives are preferably used and also easily available. As for its derivatives, those preferably used are methyl, benzyl, benzhydryl, para-nitrobenzyl, para-methoxybenzyl, para-methylbenzyl or para-bromobenzyl esters of D- or L-mandelic acid. In the Examples and Referential Examples given below, D-mandelic acid, its derivative or their residues are abbreviated as D-Mande in some cases, and L-mandelic acid, its derivative or their residues are abbreviated as L-Mande in some cases.

The following Examples and Referential Examples illustrate this invention in more detail, which are not intended, however, to limit the scope of this invention.

Abbreviations used in these Examples and Referential Examples have the following meaning:

| Me | Methyl, | $CH_2Ph$ | Benzyl, |
|---|---|---|---|
| Et | Ethyl, | $CHPh_2$ | Benzhydryl, |
| Bu | Butyl, | Ph | Phenyl, |
| THF | Tetrahydrofuran, | | |
| DMF | Dimethylformamide, and | | |
| PMB | 4-Methoxybenzyl, | | |

EXAMPLE 1

Step 1

Preparation of (1S,2R,3S,4R)-bicyclo[2,2,1]hept-5-en-2,3-dicarboxylic acid, 2-(benzyl-D-mandelate) ester (II2-Del)

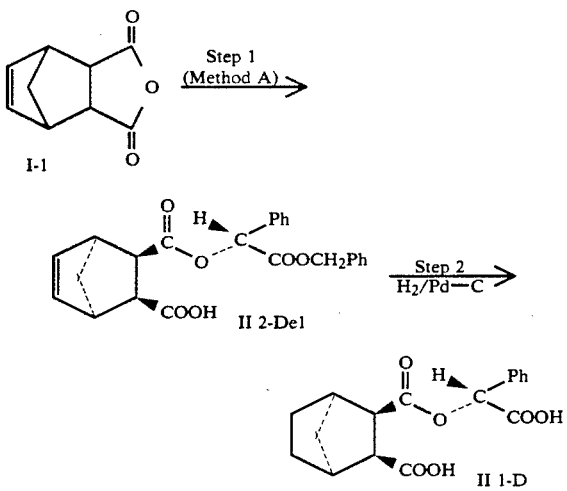

In an atmosphere of nitrogen, a solution of benzyl ester of D-mandelic acid (5.33 g, 22.0 mmol) in THF (50 ml) was cooled to −78° C. and n-BuLi (1.6M in hexane, 13.13 ml, 21.0 mmol) was added dropwise thereto. The mixture was stirred for 15 minutes and was added a solution of bicyclo[2,2,1] hept-5-en-2-endo, 3-endodicarboxylic anhydride (I-1) (3.32 g, 20.0 mmol) in THF (20 ml) thereto. The mixture was stirred for 1 hour at −78° C., and 2N hydrochloric acid was added. The reaction mixture was extracted with ethyl acetate. The organic layer was washed with water and brine and then concentrated to give compound (II2-Del) and by-product (II2'-Del) (total yield: 9.33 g). The compound (II2-Del) was purified by column chromatography on silica gel (toluene/ethyl acetate).

IR(film) ν max: 3600–2400, 1748, 1710, 1498, 1456, 1342, 1257, 1208, 1165, 1084, 1072, 912, 732, 696 cm$^{-1}$.

$^1$H-NMR(CDCl$_3$-TMS) δ ppm: 1.33(ABq, Apart, J=8.9 Hz, 1H), 1.48 (ABq, Bpart, J=8.9 Hz, 1H), 3.16(br. s, 1H), 3.21 (br. s, 1H), 3.30(dABq, Apart, J=3.2, 10 0.2 Hz, 1H), 3.47(dABq, Bpart, J=3.4 Hz, 10.2 Hz, 1H), 5.13(s, 2H), 5.97(s, 1H), 6.11(dABq, Apart, J=2.9 Hz, 5.9 Hz, 1H), 6.28(dABq, Bpart, J=2.8, 5.9 Hz, 1H), 7.13~7.52(m, 10H).

Step 2

Preparation of (1R,2R,3S,4S)-bicyclo[2,2,1]hept-2,3-dicarboxylic acid, 2-(D-mandelic acid) ester (II1-D)

To 10% palladium carbon (0.4 g) was added a solution of the previously obtained crude product (II 2-DEl) (4.06 g, 10.0 mmol) in methanol (30 ml) and the mixture was stirred for 1.5 hours at room temperature in an atmosphere of hydrogen. After the catalyst was removed by filtration, the filtrate was concentrated. The residue was partitioned between ethyl acetate and 5% aqueous solution of sodium hydrogencarbonate. The aqueous layer was separated and the organic layer was extracted with water again. The aqueous layer were combined and washed with ethyl acetate. Then, 2N hydrochloric acid was added and the mixture was extracted with ethyl acetate, washed with saturated brine, and concentrated to give the crude product (II 1-D) (3.14 g, yield from the acid anhydride: 99%, (II 1-D):(II 1'-D)=86:14 (by HPLC)). By recrystallization from ethyl acetate, the objective compound (II 1-D) was isolated (2.05 g, yield: 64%). m.p. 164°–166° C.

Anal. Calcd. (%) for C$_{17}$H$_{18}$O$_6$: C, 64.13; H, 5.71; Found (%): C, 63.83; H, 5.73

$^1$HNMR (CDCl$_3$, TMS) δ ppm: 1.46(br. s, 4H), 1.57~1.75(m, 1H), 1.84~2.08(m, 1H), 2.40~2.62(m, 2H), 3.02(dABq, Apart, J=3.6, 11.6 Hz, 1H), 3.29(dABq, Bpart, J=4.4, 11.6 Hz, 1H), 5.86(s, 1H), 7.33~7.65(m, 5H).

$[\alpha]_D$= −117.1°±0.8° (MeOH, C=1.934%, 25° C.)

The mother liquor was concentrated and the residue was recrystallized from methylene chloride to give the by-product (II 1'-D). m.p. 157°–158° C.

Anal. Calcd. (%) for C$_{17}$H$_{18}$O$_6$: C, 64.13; H, 5.71; Found (%): C, 64.02; H, 5.57.

$^1$HNMR(CDCl$_3$-TMS) δ ppm: 1.30~1.66(m, 4H), 1.69~1.87(m, 1H), 1.96~2.13(m, 1H), 2.60(br. s, 2H), 3.04(dABq, Apart, J=2.8, 12.1 Hz, 1H), 3.13(dABq, Bpart, J=3.8, 12.1 Hz, 1H), 5.84(s, 1H), 7.33~7.58(m, 5H).

$[\alpha]_D$= −81.8°±0.6° (MeOH, C=2,005%, 25° C.).

EXAMPLE 2

Preparation of (1S,2R,3S,4R)-bicyclo[2,2,1]hept-5-en-2,3-dicarboxylic acid, 2-(D-mandelic acid) ester (II 2-D)

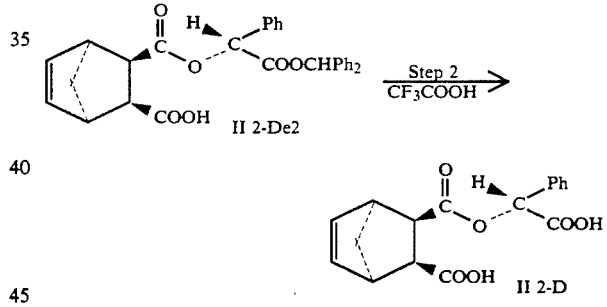

A solution of the compound (II 2-De2) (43 g) obtained by the same procedure as Example 1, Step 1 in methylene chloride (60 ml) was cooled to 0° C. Anisole (18 ml) and trifluoroacetic acid (50 ml) were added thereto and the mixture was stirred for 1 hour. The reaction mixture was concentrated and the residue was partitioned between ethyl acetate and 5% aqueous solution of sodium hydrogencarbonate. The aqueous layer was separated, washed with ethyl acetate and then acidified with 2N hydrochloric acid. The mixture was extracted with ethyl acetate, washed with saturated brine, then dried and concentrated to give the crude product (II 2-D) (Yield ratio, (II 2-D): (II 2'-D)=74:26 (by HPLC)). The product was recrystallized from ethyl acetate to give the pure objective compound (II 2-D) (13.37 g, yield: 47%). m.p. 169°–171° C.

Anal. Calcd. (%): for C$_{17}$H$_{18}$O$_6$: C, 64.55; H, 5.10; Found (%): C, 64.46; H, 5.12.

IR(CHCl$_3$) ν max: 3500–2400, 1734, 1438, 1375, 1342, 1256, 1168, 1146, 1072 cm$^{-1}$.

$^1$HNMR(CDCl$_3$-TMS) δ ppm: 1.36(ABq, Apart, J=7.2 Hz; 1H), 1.51 (ABq, Bpart, J=7.2 Hz, 1H), 3.15(br, s, 2H), 3.43(dABq, Apart, J=2.9, 10.4 Hz, 1H), 3.53(dABq, Bpart, J=3.1, 10.4 Hz, 1H), 5.86(s, 2H), 6.14~6.33(m, 2H), 7.32~7.62(m, 5H).

[α]$_D$= −159.5°35 1.0° (MeOH, C=1.993%, 24° C.)

EXAMPLES 3-6

By the same procedures as described in Examples 1 and 2, the objective compounds (II-D) or (II-L) as shown in Table 1 were obtained. The reaction conditions were also shown in Table 1.

EXAMPLE 7

Preparation of (1R, 2S, 3R, 4S)-bicyclo[2.2.1]hepta-5-en-2,3-dicarboxylic acid, 2-(D-mandelate) ester (II 2-L)

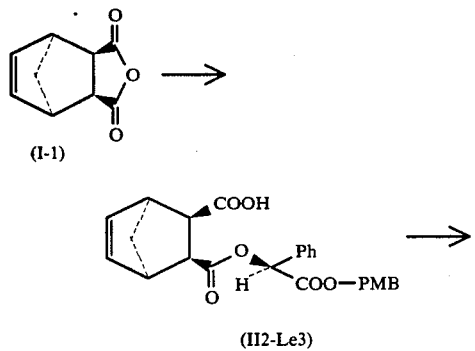

(I-1)

(II2-Le3)

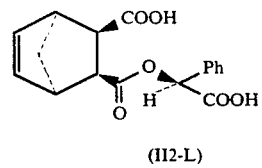

(II2-L)

By the same procedure as in Step 1 of Example 1, the crude product (II2-Le3) shown in Table 1 was prepared. The reaction conditions are also shown in Table 1.

To a solution of 30.6 g (70 mmol) of the above crude product (II 2-Le3) in 160 ml of acetonitrile was added 35.9 ml (70 mmol×6) of conc. hydrochloric acid and the mixture was stirred for 16 hours at room temperature. The reaction mixture was adjusted to pH 4 with 4N NaOH, then made alkaline with an aqueous sodium hydrogencarbonate under ice-cooling, and then washed with ethyl acetate. The organic layer was further extracted with water and the combined aqueous layer was acidified with conc. hydrochloric acid to pH 2 and extracted with ethyl acetate. The organic layer was washed with water, dried over anhydrous sodium sulfate, concentrated under reduced pressure to give a crystalline residue. The crude product was recrystallized with ethyl acetate to give 11.2 g of the compound (II 2-L) in 50.2% yield.

mp. 168° to 170° C.

The IR and $^1$NMR data of the compound (II 2-L) were identical with those of compound (II 2-D), respectively.

[α]$_D$= +160.5°±1.0° (MeOH, 23° C., c=2.002%)

TABLE 1

| | Compound (I) | | D-Mande or L-Mande | | | Crude Product Yd.: g (Yd.: %) | | |
|---|---|---|---|---|---|---|---|---|
| Ex. No. | R¹ R² / X / R¹ R² | Amount g (mmol) | D- L- | R³ | Ar M¹ | Amount g (mmol) | Producing ratio: (II-D:II'-D) or (II-L:II'-L) | Deprotection | Aimed Compound (II) |
| 3 | (norbornyl) | 47.6 (286) | D- | Me | Ph Li | 47.6 (286) | 91 g (96%) *1 (82:18) | | |
| 4 | (norbornyl) | 1.66 (10.0) | D- | H | Ph Li | 1.52 (10.0) | 2.57 g (81%) (50:50) | — | II$^{1\text{-}D}$ |
| 5 | (norbornyl) | 14.39 (86.6) | L- | CHPh₂ | Ph Li | 30.35 (95.3) | 26.5 g (96%) (73:27) | Pd—C | II$^{1\text{-}L}$ *2 |

TABLE 1-continued $$R^1 \underset{R^2}{\overset{X}{\underset{R^1}{\bigvee}}} \underset{R^2}{\overset{O}{\underset{O}{\bigvee}}} \xrightarrow{\text{D-Mande or L-Mande}} \text{II-D or II-L}$$

I

| | Compound (I) $R^1 \underset{R^2}{\overset{X}{\underset{R^1}{\bigvee}}} R^2$ | | D-Mande or L-Mande | | | | Crude Product Yd.: g (Yd.: %) Producing ratio: (II-D:II'-D) or | | Aimed |
|---|---|---|---|---|---|---|---|---|---|
| Ex. No. | | Amount g (mmol) | D- L- | $R^3$ | Ar | $M^1$ | Amount g (mmol) | (II-L:II'-L) | Deprotection | Compound (II) |
| 6 | ⌬ | 1.42 (8.68) | D- | $CH_2C_6H_4OMe$ | Ph | Li | 2.59 (9.51) | 2.04 g (74%) (82:18) | Pd—C | $II^{1-D}$ |
| 7 | ⌬ | 11.50 (70.0) | L- | $CH_2C_6H_4OMe$ | Ph | Li | 20.97 (77.0) | 21.8 (98%) (85:15) | HCl | $II^{2-L}$ *3 |

Remarks)
*1 The yield and the producing ratio are shown as a methyl ester.
*2 m.p. 162–164° C., $[\alpha]_D = +113.2 \pm 1.5°$ (MeOH. C = 1.0075%, 23.5° C.)
*3 m.p. 168–170° C., $[\alpha]_D = +160.5 \pm 1.0°$ (MeOH. C = 2.002%, 23.5° C.)

EXAMPLE 8

Preparation of (1R,2S,3R,4S)-7-oxabicyclo[2.2.1]heptan-2,3-dicarboxylic acid, 2-D-mandelic acid ester (II 3-D)

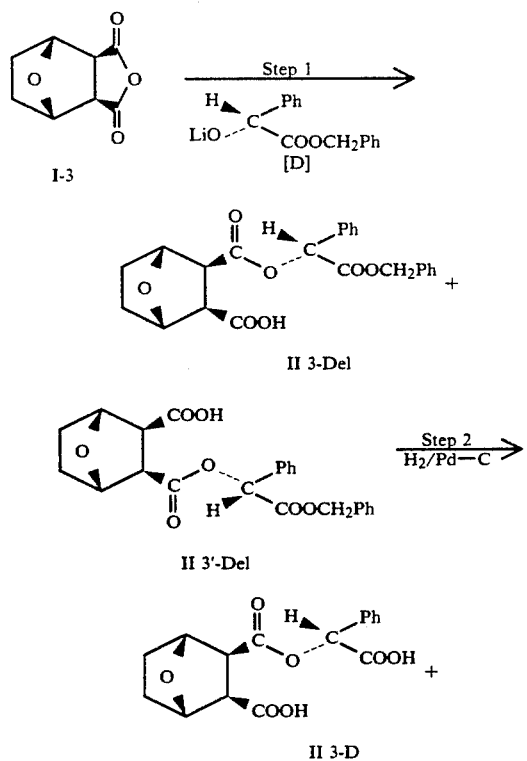

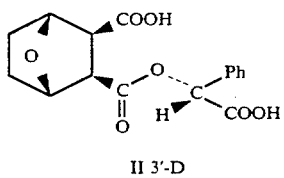

II 3'-D

According to the procedure in Step 1 and 2 in Example 1, the mixture of the compounds (II 3-D) and (II 3'-D) was prepared from 10.5 g (62 mmol) of the compound (I-3). ((II 3-D):(II 3'-D)=73:27 (by HPLC)). From the mixture, 7.1 g of the compound (II 3-D) and 1.5 g of the compound (II 3'-D) was isolated by recrystallization in 35.8% and 7.6% yield, respectively.

Compound (II 3-D)
mp. 175°–177° C.
Anal. Calcd. (%) for $C_{16}H_{16}O_7$: C, 59.99; H, 5.04; Found (%): C, 59.85; H, 5.04.
$^1$HNMR(CD$_3$OD-TMS) δ ppm: 1.55~1.88(m,4H), 3.13(ABq, A-part, J=9.6 Hz, 1H), 3.19(ABq, B-part, J=9.6 Hz, 1H), 4.83~4.90(m, 2H), 5.85(s,1H), 7.35~7.65(m,5H).
IR(Nujol) ν max: 3480~2200, 1733, 1712, 1659, 1229, 1220, 1185, 1011, 969, 936, 766, 735, 696 cm$^{-1}$.
$[\alpha]_D-111.9°\pm1.5°$ (MeOH, 23° C., C=1.013%)
Compound (II 3'-D)
mp. 133°–135° C.
Anal. Calcd. (%) for $C_{16}H_{16}O_7.O$ 0.5H$_2$O: C, 58.35; H, 5.21; Found (%): C, 58.33; H, 5.48.
$^1$HNMR(CD$_3$OD-TMS) δ ppm: 1.55~1.90(m,4H), 3.12(ABq, A-part, J=9.6 Hz, 1H), 3.22(ABq, B-part, J=9.6 Hz, 1H), 4.75~4.90(m, 2H), 5.74(s, 1H), 7.35~7.65(m, 5H).

IR(Nujol) ν max: 3680~2200, 1733, 1710(sh), 1230, 1177, 1044, 994, 925, 819, 724 cm$^{-1}$.
[α]$_D$ −92.0°±1.3° (MeOH, C=1.014%, 23° C.).

EXAMPLE 9

Step 1

Preparation of (3R)-3-[(tert-butyldimethylsilyl)oxy]glutaric acid, 1-(benzyl D-madelate) ester (II 4-D)

In a nitrogen atmosphere, to a solution of 24.23 g (100 mmol) of benzyl D-mandelate in 480 ml of THF was cooled to −78° C. and 66 ml (106 mmol) of 1.6M n-BuLi in hexane was added dropwise thereto. The mixture was stirred for 20 minutes. To the reaction mixture was added a solution of 24.44 g (100 mmol) of 3-[(tert-dimethylsilyl)oxy]glutaric anhydride (I-4) in 100 ml of THF. The resulting mixture was stirred for 2 hours at −78° C. and the reaction mixture was treated with 1N hydrochloric acid and extracted with ethyl acetate. The organic layer was washed with water and an aqueous solution of sodium chloride, concentrated to give a mixture of the compound (II 4-Del) and the by-product (II 4'-Del) in the ratio of 5:1 (by $^1$HNMR).

Rf=0.29 (chloroform:methanol=10:1)

$^1$H-NMR(CDCl$_3$, TMS) δ ppm: 0.03(s, 3H), 0.05 (s, 3H), 0.82(s, 9H), 2.61~2.68(m, 4H), 4.53~4.63(m, 1H), 5.10(ABq, Apart, J=12.5 Hz), 5.17(ABq, Bpart, J=12.5 Hz), 5.98(s, 1H), 7.17~7.48(m, 10H).

Step 2

Preparation of (3R)-3-[(tert-butyldimethylsilyl)oxy]glutaric acid, 1-D-mandelic acid ester (II 4-D)

To 500 ml of solution of the crude product prepared in Step 1 (mixture of the compounds (II 4-Del) and (II 4'-Del)) in ethyl acetate was added 1.00 g of 5% palladium-carbon and the mixture was stirred for 1 hour at room temperature in a hydrogen atmosphere. The catalyst was removed by filtration and the filtrate was concentrated to give the crude (II 4-D). The crude product was recrystallized from diethyl ether-hexane to give 22.53 g of the aimed compound (II 4-D) in 57% yield. mp. 141°-142° C.

Anal. Calcd. (%) for C$_{19}$H$_{28}$O$_7$Si: C, 57.55; H, 7.12; Found (%): C, 57.39; H, 7.08.

IR(KBr) ν max: 3700~2400, 1735, 1712, 1253, 1188, 1167, 1080, 980, 832 cm$^{-1}$.
$^1$H-NMR(CDCl$_3$, TMS) δ ppm: 0.04(s, 3H), 0.05(s, 3H), 0.82(s, 9H), 2.53~2.84(m, 4H), 4.53~4.66(m, 1H), 5.95(s, 1H), 7.38~7.49(m, 5H).
[α]$_d$= −70.2°±1.1° (CHCl$_3$, C=1.008%, 23.4° C.)
Rf=0.82(ethyl acetate:acetic acid:water=30:1:1)

REFERENTIAL EXAMPLE 1

Method for Preparing Arylacetic Acid Derivatives

Preparation of benzyl ester of D-mandelic acid

A solution of D-mandelic acid (85.1 g, 559 mmol), benzyl alcohol (65 ml, 628 mmol) and p-toluene-sulfonic acid (1.01 g, 5.35 mmol) in benzene (700 ml) is refluxed for 6.5 hours and the reaction mixture is washed with water, and then concentrated. The residue is recrystallized from ether to give 123.5 g of the titled compound. Yield: 91%. m.p. 103.5°-105° C.

Anal. Calcd. (%) for C$_{15}$H$_{14}$O$_3$: C, 74.36; H, 5.82; Found (%): C, 74.53; H, 5.90.

$^1$HNMR(CDCl$_3$-TMS) δ ppm:3.44(d, J=5.6 Hz, 1H), 5.14(ABq, Apart, J=12.3 Hz, 1H), 5.22(d, J=5.6 Hz, 1H), 5.24 (ABq, Bpart, J=12.3 Hz, 1H) 7.15~7.50 (m, 10H).

[α]$_D^{24}$= −55.7 °±1.0° (CHCl$_3$, C=1.003%).

Preparation of 4-methoxybenzyl ester of D-mandelic acid

A solution of D-mandelic acid (15.3 g, 100 mmol), 4-methoxybenzyl alcohol (15.2 g, 110 mmol) and p-toluene-sulfonic acid (0.197 g, 1.01 mmol) in benzene (300 ml) is refluxed for 7 hours, and the reaction mixture is washed with water (4 times), and then concentrated. The crude product obtained is purified by column chromatography on silica gel eluted with toluene/ethyl acetate. The product is recrystallized from ether/petroleum ether to give 6.58 g of the titled compound. Yield: 24%. m.p. 70.5°-73.5° C.

Anal. Calcd. (%) C$_{16}$H$_{16}$O$_4$: C, 70.58; H, 5.92; Found (%): C, 70.55; H, 6.00.

$^1$HNMR(CDCl$_3$-TMS) δ ppm: 3.80(s, 3H), 5.05 (ABq, Apart, J=11.8 Hz, 1H), 5.19(s, 1H), 5.19(ABq, Bpart, J=11.8 Hz, 1H), 6.84 (d, J=8.7 Hz, 2H), 7.17(d, J=8.7 Hz, 2H), 7.30~7.45(m, 5H).

[α]$_D$= −36.0±0.8 (CHCl$_3$, C=1.017%, 24° C.).

Preparation of 4-nitrobenzyl ester of D-mandelic acid

A solution of D-mandelic acid (15.2 g, 100 mmol), 4-nitrobenzyl bromide (21.6 g, 100 mmol) and triethylamine (14.0 ml, 100 mmol) in DMF (300 ml) is stirred for 8 hours at room temperature. The reaction mixture, to which is added water is extracted with ethyl acetate and the organic solution is washed with diluted hydrochloric acid and water. The resulting product is recrystallized from ether/petroleum ether to give 19.6 g of the titled compound. Yield: 68%. m.p. 143°-145° C.

Anal. Calcd. (%) for C$_{15}$H$_{13}$NO$_5$: C, 62.72; H, 4.56; N, 4.88; Found (%): C, 62.76; H, 4.61; N, 4.99.

$^1$HNMR(CDCl$_3$-TMS) δ ppm: 3.26~3.52(br. s, 1H), 5.25(ABq, Apart, J=13.5 Hz, 1H), 5.28(s, 1H), 5.32(ABq, Bpart, J=13.5 Hz, 1H), 7.27(d, J=8.4 Hz, 2H), 7.34~7.48(br. s, 5H), 8.14(d, J=8.4 Hz, 2H)

[α]$_D^{24}$= −40.0°±0.8° (CHCl$_3$, C=0.995%)

Preparation of benzhydryl ester of D-mandelic acid

To a solution of D-mandelic acid (25.0 g, 164 mmol) in ethyl acetate (200 ml) is added diphenyldiazomethane (38.9 g, 164 mmol) with stirring at room temperature. After completion of the reaction is monitored by TLC, the reaction mixture is concentrated. The residue is recrystallized from ether/petroleum ether to give 47.7 g of the titled compound. Yield: 91%. m.p. 91°-91.5° C.

Anal. Calcd. (%) for $C_{21}H_{18}O_3$: C, 79.22; H, 5.71; Found (%): C, 79.44; H, 5.67.

$^1$HNMR(CDCl$_3$-TMS) δ ppm: 3.47(d, J=5.3 Hz, 1H), 5.28(d, J=5.3 Hz, 1H), 6.87(s, 1H), 6.87~7.46(m, 15H).

$[α]_D^{24}$ = −57.4°±1.0° (CHCl$_3$, C=1.023%).

Preparation of benzhydryl ester of L-mandelic acid

The reaction using L-mandelic acid (30.4 g, 200 mmol), ethyl acetate (200 ml) and diphenyldiazomethane (38.9 g, 200 mmol) is performed in the same manner as in the fore-mentioned preparation of benzhydryl ester of D-mandelic acid to give 54.7 g (172 mmol) of the titled compound. Yield: 86%. m.p. 91.5°-92.0° C.

$[α]_D$ = +55.7°±0.9° (CHCl$_3$, C=1.013, 24° C.).

Monoesters (II-D) or II-L) of arylacetic acid obtained in this invention can be converted into pure monoesters of dicarboxylic acid (III) having optionally desired configurations by simple reactoins mentioned below:

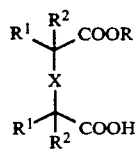

wherein R is alkyl

Reactions (1) After dialkyl esterification under neutral to acidic conditions (with the use of a methylating agent such as diazomethane or methanol with a catalytic amount of p-toluenesulfonic acid and the like), the arylacetic acid moiety is removed by hydrogenolysis.

(2) The product obtained is heated in an appropriate alcohol (methanol, etc.) in the presence of a metalic salt (NaOMe, etc.) of the said alcohol.

The following scheme shows reaction processes with the use of the compound (II 1-D) or (II 1-L):

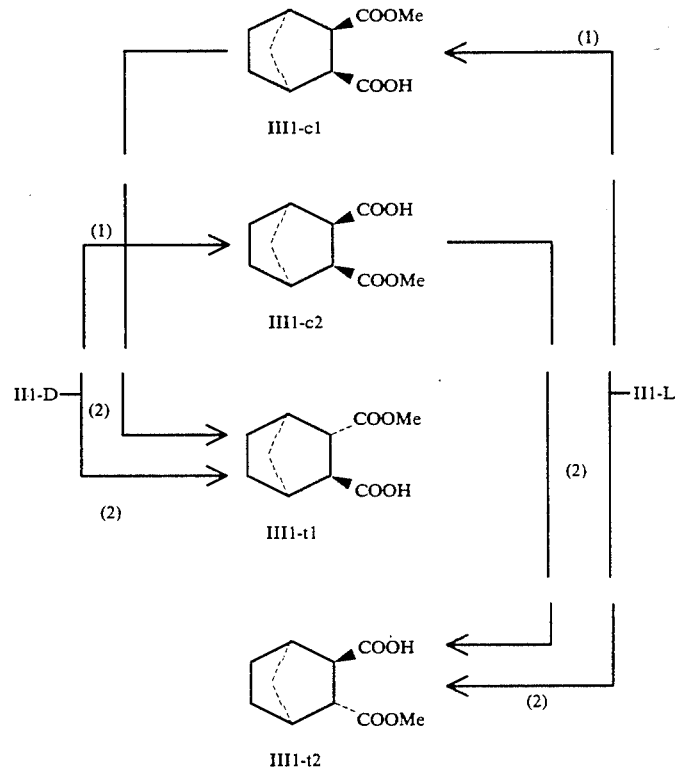

REFERENTIAL EXAMPLE 2

Using (II 1-D) as a starting material and treating by the procedure (2), the compound (III 1-t1) is obtained. Yield: 94% m.p. 59°-60° C.

Anal. Calcd. (%) for $C_{10}H_{14}O_4$: C, 60.58; H, 7.13; Found (%): C, 60.66; H, 7.08.

$^1$HNMR(CDCl$_3$-TMS) δ ppm: 1.20~1.74(m, 6H), 2.59(br. s, 1H), 2.69(br. s, 1H), 2.79(d, J=5.4 Hz, 1H), 3.27(dd, J=3.8, 5.4 Hz, 1H), 3.69(s, 3H).

$[α]_D^{25}$ = +38.4°±0.4° (MeOH, C=2.002%)

Using (II 1-L) as a starting material and treating by the procedure (2), the compound (III 1-t2) is obtained. Yield: 78% m.p. 59°-60° C.

$[α]_D^{25}$ = −38.4°±0.4° (MeOH, C=2.013%)

REFERENTIAL EXAMPLE 3

(+)-(1R,2S,3S,4S)-(5Z)-7-[3-(Phenylsulfonylamino)-bicyclo[2,2,1]hept-2-yl]heptenoic acid (hereinafter abbreviated as (+)-S-145), which is useful as thromboxane receptor antagonist, can be obtained easily from the compound (III 1-t1) by the following method:

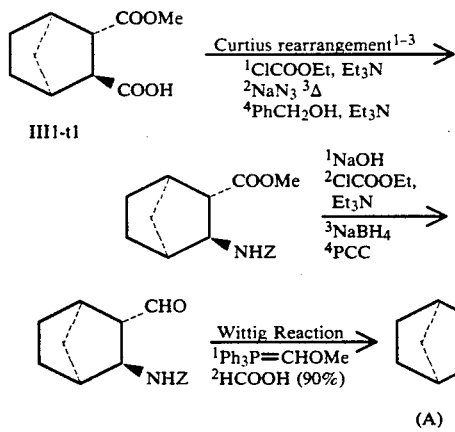

where Et is ethyl, Z is benzyloxycarbonyl, and PPC is pyridinium chlorochromate.

The compound (A) thus obtained is described in the literature (J. Med. Chem., 31(9), 1847–1854, (1988)), and (+)-S-145 is obtained from this compound by the method shown in the said literature.

We claim:

1. An ester of arylacetic acid of the formula (II):

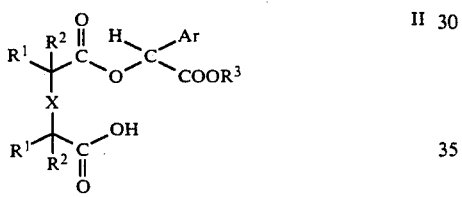

wherein $R^1$ is hydrogen or optionally substituted $C_1$–$C_2$, alkyl or phenyl or the $R^1$ groups taken together form $C_2$–$C_6$ alkylene, $C_2$ or $C_4$–$C_6$ alkenylene, or a bicyclic-ring; $R^2$ is hydrogen or methyl; X is a single bond, $CH_2$, $CHCH_3$, or $CHOR^5$ provided that when X is a single bond or $R^1$ and $R^2$ are not simultaneously hydrogen or methyl; $R^3$ is hydrogen, optionally substituted alkyl, or optionally substituted aralkyl; $R^5$ is hydrogen or hydroxy protecting group; and Ar is optionally substituted aryl.

2. A compound claimed in claim 1 wherein $R^1$ is hydrogen, $R^2$ is hydrogen, and X is $CHOR^5$.

3. A compound as claimed in claim 1 said compound being (1R,2R,3S,4S)-bicyclo[2.2.1]hept-2,3-dicarboxylic acid, 2-(D-mandelic acid) ester.

4. An asymmetric synthesis for preparing an ester of arylacetic acid of the formula (II):

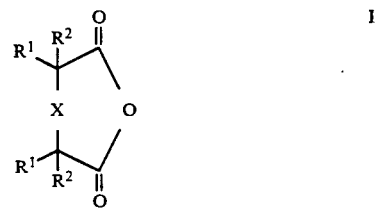

wherein $R^1$ is hydrogen or optionally substituted $C_1$–$C_2$, alkyl or phenyl or the $R^1$ groups taken together form $C_2$–$C_6$ alkylene, $C_2$ or $C_4$–$C_6$ alkenylene, or a bicyclic-ring; $R^2$ is hydrogen or methyl; X is a single bond, $CH_2$, $CHCH_3$ or $CHOR^5$ provided that when X is a single bond or $R^1$ and $R^2$ are not simultaneously hydrogen or methyl; $R^3$ is hydrogen, optionally substituted alkyl, or optionally substituted aralkyl; $R^5$ is hydrogen or hydroxy protecting group; and Ar is optionally substituted aryl, which comprises reacting a σ symmetric acid anhydride of the formula (I):

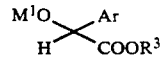

wherein $R^1$, $R^2$ and X, each has the meaning as defined above, with an (R)- or (S)-arylacetic acid derivative of the formula $$M^1O \quad Ar$$
$$H \quad COOR^3$$

wherein $M^1$ is hydrogen or metal atom and $R^3$ and Ar each has the same meaning as defined above.

5. An asymmetric synthesis as claimed in claim 4 wherein $R^1$ is hydrogen, $R^2$ is hydrogen, and X is $CHOR^5$.

* * * * *